(12) United States Patent
Nishide et al.

(10) Patent No.: US 8,088,121 B2
(45) Date of Patent: Jan. 3, 2012

(54) CATHETER

(75) Inventors: Takuji Nishide, Settsu (JP); Osamu Kikugawa, Kanagawa (JP); Shogo Miki, Tokyo (JP)

(73) Assignee: Kaneka Corporation, Osaka-Shi (JP)

( * ) Notice: Subject to any disclaimer, the term of this patent is extended or adjusted under 35 U.S.C. 154(b) by 603 days.

(21) Appl. No.: 11/573,549

(22) PCT Filed: Jul. 29, 2005

(86) PCT No.: PCT/JP2005/013982
§ 371 (c)(1),
(2), (4) Date: Jun. 23, 2009

(87) PCT Pub. No.: WO2006/016491
PCT Pub. Date: Feb. 16, 2006

(65) Prior Publication Data
US 2009/0270802 A1    Oct. 29, 2009

(30) Foreign Application Priority Data
Aug. 11, 2004 (JP) ................................. 2004-234651

(51) Int. Cl.
*A61M 25/00* (2006.01)
*A61M 29/00* (2006.01)

(52) U.S. Cl. .............. 604/525; 604/102.02; 604/103.04; 604/264; 604/524; 604/915

(58) Field of Classification Search ............. 604/103.04, 604/103.05, 93.01, 96.01, 102.01, 102.02, 604/103.09, 264, 523, 524, 525, 533, 534, 604/915
See application file for complete search history.

(56) References Cited

U.S. PATENT DOCUMENTS

| | | | | |
|---|---|---|---|---|
| 4,748,982 A * | 6/1988 | Horzewski et al. | ........... | 606/192 |
| 5,333,620 A * | 8/1994 | Moutafis et al. | ............... | 600/585 |
| 5,389,087 A * | 2/1995 | Miraki | ........................... | 604/247 |
| 5,658,251 A * | 8/1997 | Ressemann et al. | ........ | 604/96.01 |
| 6,066,114 A * | 5/2000 | Goodin et al. | ........... | 604/103.04 |
| 2004/0006360 A1 * | 1/2004 | Garakani | ....................... | 606/192 |

FOREIGN PATENT DOCUMENTS

| | | |
|---|---|---|
| JP | 02-277465 | 11/1991 |
| JP | 06-507105 | 8/1994 |
| JP | 09-503411 | 4/1997 |
| JP | 2003-102841 | 4/2003 |
| JP | 2003-517897 | 6/2003 |
| JP | 2003-517901 | 6/2003 |

* cited by examiner

*Primary Examiner* — Nicholas Lucchesi
*Assistant Examiner* — Leah Stohr
(74) *Attorney, Agent, or Firm* — Kratz, Quintos & Hanson, LLP

(57) ABSTRACT

A catheter enabling an increase in operability when the catheter is inserted from the outside to the inside of a body and capable of remarkably reducing the risk of damage to shafts even in an unforeseen accident without complicating steps and increasing production cost. The catheter comprises at least the distal side shaft formed of a resin tube, the rear end side shaft with a higher rigidity than that of the distal side shaft, and a guide wire lumen. The catheter is characterized in that a core wire is disposed therein to adjust a flexibility so that the rear end portion of the distal side shaft is harder than the distal end portion of the distal side shaft and softer than the rear end side shaft, and the core wire is fixed to the distal side shaft near the rear end side opening part of the guide wire lumen and at a part of the rear end side portion of the distal end shaft.

8 Claims, 15 Drawing Sheets

CATHETER

TECHNICAL FIELD

The present invention relates to a catheter for use in medical application, and in particular, to a balloon catheter for use in peripheral angioplasty and percutaneous transluminal angioplasty (PTA, or percutaneous transluminal coronary angioplasty, PTCA) during coronary angioplasty, valve repair, or the like, a penetrating catheter for penetration through a stenotic lesion, an injection catheter allowing administration of a treatment substance to a local site, and the like.

BACKGROUND ART

Percutaneous transluminal angioplasty has been practiced widely, for example, for treatment of stricture or obstruction of vascular lumen by enlargement and for recovery or improvement of blood flow in coronary and peripheral blood vessels. The balloon catheter used in the percutaneous transluminal angioplasty has a shaft and a balloon inflation and deflation freely by regulation of its internal pressure that is connected to the terminal region of the shaft, and the shaft generally has a structure in which a lumen (guide wire lumen) for inserting a guide wire and a lumen for supplying a pressurized fluid for regulation of the balloon internal pressure (inflation lumen) are formed in the shaft in the length direction.

The PTCA by using such a balloon catheter is generally practiced as follows: First, a guide catheter is inserted from a puncture site such as femoral artery, brachial artery, or radial artery, while the distal end is fed via aorta into the entrance of coronary artery. Then, a guide wire inserted in the guide wire lumen is fed beyond the stenotic lesion of coronary artery, and a balloon catheter is then inserted along the guide wire, while the balloon is delivered to the stenotic lesion. Then, the stenotic lesion is dilated and treated by expansion of the balloon by supply of a pressurized fluid via the inflation lumen by a device such as inflator. After completion of the treatment of the stenotic lesion by dilation, the PTCA is completed by contracting the balloon under reduced pressure and withdrawing it out of the body.

In the cases of a lesion significantly higher in the degree of stricture or of chronic complete obstruction, it is occasionally difficult to treat the lesion by advancing the guide wire beyond the stenotic lesion. In such a case, a penetrating catheter is used, and the guide wire is sent beyond the stenotic lesion.

It is often necessary to administer a treatment substance locally to the stenotic lesion during PTCA. An example thereof is the treatment for dissolving thrombus by local administration of a thrombolytic agent. In such a case, an injection catheter is used for local administration of the treatment substance.

Each catheter described above has a structure in which a distal-end-sided shaft and a proximal-end-sided shaft are connected to each other and a hub holding the catheter is connected to the proximal end of the proximal-end-sided shaft, and such catheters are divided roughly into two groups, depending on the length of the guide wire lumen. Hereinafter, a common balloon catheter having a balloon connected to the distal end side of a distal-end-sided shaft and to the hub and a port for supplying a pressurized fluid for regulation of the internal pressure of the balloon will be described as an example.

An example of the catheter is an over-the-wire catheter (OTW catheter) shown in FIG. 1, in which a guide wire lumen is formed over the entire length of the catheter, a proximal opening of the guide wire lumen is formed in the hub, and a distal opening of the guide wire lumen is formed in the most distal end region or at a position to the terminal side of the most distal end region. Another example thereof is a rapid exchange catheter (RX catheter) shown in FIG. 2, in which a guide wire lumen is present only in the distal end side of balloon catheter and a proximal opening of the guide wire lumen is formed in the middle of the distal-end-sided shaft. Because the OTW catheter has a guide wire lumen over the entire length of the balloon catheter, it is often used for sending a guide wire to the lesion that prohibits passage of the guide wire, but the operation of withdrawing the balloon catheter while leaving the guide wire in the lesion is rather complicated and causes problems. Thus, the OTW catheter demands additional special device and operation such as insertion of an exchange extension wire for withdrawal of the balloon catheter while the guide wire is left in the lesion.

On the other hand, in the RX catheter, the guide wire lumen is present only in the distal end side of the balloon catheter; thus, the convenience of operation is very favorable, as it is possible to remove, reinsert the balloon catheter easily while leaving the guide wire in the lesion; and it is also possible to shorten the surgical period and reduce the number of devices used.

Exemplified above is a balloon catheter having a balloon in the distal end side of the distal-end-sided shaft, but the characteristics of the OTW and RX catheters are not limited to the balloon catheter, and are also common to penetrating catheters for stricture penetration, injection catheters for administration of a treatment substance, and other catheters. The present invention relates to such a RX catheter.

Various methods for improving the convenience in operating the RX catheter are disclosed.

Patent Document 1 discloses a balloon dilation RX catheter having an opening of guide wire lumen in the region between the middle region and the base region, wherein, when the guide wire is placed in the guide wire lumen, the catheter is supported thereby continuously over the entire length in the length direction.

The catheter disclosed in the prior art is favorable in convenience of operation, because the catheter is supported continuously in the longitudinal direction when the guide wire is placed, but disadvantageously, the change in rigidity of the catheter itself in the length direction is discontinuous, and thus, when the catheter is inserted into the body from outside along the guide wire, the catheter is easily broken at the connection region between the middle region and the base region, and thus, it is extremely low in the convenience of operation.

Alternatively, Patent Document 2 discloses an intravascular catheter, comprising a metal-tube main shaft, a balloon, a plastic shaft region between the main shaft and the balloon, an intermediate unit not harder than the main shaft region that is connected to the main shaft and extending in the plastic shaft region in the proximal terminal direction, and a guide wire lumen, wherein the inlet of the guide wire is formed at a position separated in the proximal terminal direction from the proximal terminal of the main shaft region.

The prior art discloses a catheter improved in slidability and shape compatibility; the convenience of operation when a catheter is inserted into the body along the guide wire from outside is also improved; but there is still a problem in production cost. Such a catheter demands an additional step of brazing, laser bonding, or the like for connecting the intermediate unit not harder than the main shaft region to the main shaft, causing problems of increase in production cost by installation of a large-scale facility, complication of processing, and others.

Yet alternatively, Patent Document 3 discloses a dilation catheter having a stylet allowing improvement in the compression strength of the catheter shaft and the transmission (insertion) efficiency of the force in the axial direction.

In this prior art, presence of the stylet leads to improvement in force transmission (insertion) in the axial direction and also in the convenience of operation when the catheter is inserted into the body along the guide wire from outside; but the catheter has a structure in which the proximal terminal of the stylet terminates at the hub unit including the proximal terminal region of catheter shaft; and thus, when it is a balloon catheter, the stylet is present in most of the inflation lumen, and disadvantageously, the response of the balloon to inflation and deflation becomes lower. Alternatively when the catheter is an injection catheter, the stylet is present in most of the infusion lumen (lumen for injection of a treatment substance), disadvantageously reducing the convenience of operation in injecting a treatment substance.

Patent Document 4 discloses a RX balloon catheter having a proximal-end-sided shaft of metal tube, having a structure in which the core wire for adjustment of flexibility is connected to the distal-end-sided shaft only in the area close to the proximal opening of the guide wire lumen.

In this prior art, the convenience of operation when a catheter is inserted into the body along a guide wire and the response of the balloon to inflation and deflation are improved, without complication of processing or increase in production cost. However, the catheter described in this prior art has a structure in which the core wire is connected to the distal-end-sided shaft only in the area close to the proximal opening of the guide wire lumen, and thus, it is not possible to exclude the possibility of the following shaft damage. Namely when the lubricity between the guide wire and the balloon catheter during use of the balloon catheter drops drastically, for example, by deposition of thrombus, if a force is applied to the proximal-end-sided shaft for sliding or withdrawal of the balloon catheter, a tension in the axial direction is applied to the balloon catheter itself. Although the possibility is quite low, there is still very small possibility that the proximal end of the distal-end-sided shaft is elongated and deformed by the tension and the proximal end of the core wire present in the proximal-end-sided shaft may move to the proximal end of the distal-end-sided shaft. Accordingly, there is still a possibility of the damage of the proximal end of the distal-end-sided shaft elongated or deformed by the proximal end of the core wire and the damage, for example of blood vessel, by the proximal end of the core wire penetrating through proximal end of the distal-end-sided shaft, although it is quite rare.

Patent Document 1: Japanese Examined Patent Publication No. 5-28634
Patent Document 2: Japanese Unexamined Patent Publication No. 6-507105
Patent Document 3: Japanese Unexamined Patent Publication No. 9-503411
Patent Document 4: Japanese Unexamined Patent Publication No. 2003-102841

DISCLOSURE OF THE INVENTION

Technical Problems to be Solved

Thus, an object of the present invention, which was made in view of the problems above, is to provide a catheter improved in the convenience of operation when the catheter is inserted into the body along a guide wire from outside that is resistant to excessive elongation and deformation of the shaft even under unexpected condition and eliminates the concern about the damage of the shaft, blood vessel, or the like by the proximal end of the core wire without complication of processing or increase in production cost.

Means to Solve the Problems

After intensive studies to solve the problems above, the inventors have invented a catheter, comprising a distal-end-sided shaft of resin tube, a proximal-end-sided shaft more rigid than the distal-end-sided shaft, and a guide wire lumen allowing incorporation of a guide wire inside and having a distal opening and a proximal opening, wherein: the guide wire lumen forms the distal opening in the most distal end region of the catheter and the proximal opening in the middle of the distal-end-sided shaft; the distal end region of the proximal-end-sided shaft is connected to the proximal terminal of the distal-end-sided shaft; the distal-end-sided shaft includes the distal-end-sided shaft proximal region and the distal-end-sided shaft distal region; a core wire for adjustment of the flexibility of the distal-end-sided shaft proximal region is so placed in the catheter that the distal-end-sided shaft proximal region becomes harder than the distal-end-sided shaft distal region and softer than the proximal-end-sided shaft; and the core wire is connected to the distal-end-sided shaft in the area close to the proximal opening of the guide wire lumen and in part of the distal-end-sided shaft proximal region.

Thus, the present invention (1) relates to a catheter, comprising a distal-end-sided shaft of resin tube, a proximal-end-sided shaft more rigid than the distal-end-sided shaft, and a guide wire lumen allowing incorporation of a guide wire inside and having a distal opening and a proximal opening, wherein: the guide wire lumen forms the distal opening in the most distal end region of the catheter and the proximal opening in the middle of the distal-end-sided shaft; the distal end region of the proximal-end-sided shaft is connected to the proximal terminal of the distal-end-sided shaft; the distal-end-sided shaft includes the distal-end-sided shaft proximal region and the distal-end-sided shaft distal region; a core wire for adjustment of the flexibility of the distal-end-sided shaft proximal region is so placed in the catheter that the distal-end-sided shaft proximal region becomes harder than the distal-end-sided shaft distal region and softer than the proximal-end-sided shaft; and the core wire is connected to the distal-end-sided shaft in the area close to the proximal opening of the guide wire lumen and in part of the distal-end-sided shaft proximal region.

The present invention (2) relates to the catheter according to (1), wherein the proximal opening of the guide wire lumen is present between the distal-end-sided shaft distal region and the distal-end-sided shaft proximal region.

The present invention (3) relates to the catheter according to (1) or (2), wherein the core wire is connected to the internal surface of the distal-end-sided shaft as it is covered with a thermoplastic resin layer in the area where the core wire is connected to the distal-end-sided shaft.

The present invention (4) relates to the catheter according to any one of (1) to (3), wherein the core wire has a distal end region, which is located to the distal end side of the proximal opening of the guide wire lumen.

The present invention (5) relates to the catheter according to any one of (1) to (4), wherein the core wire has a proximal terminal, which is located inside the proximal-end-sided shaft and to the distal end side by a particular length of the proximal terminal of the proximal-end-sided shaft.

The present invention (6) relates to the catheter according to any one of (1) to (5), wherein at least part of the core wire in the region corresponding to the distal-end-sided shaft proximal region has a tapered shape with its external diameter gradually decreasing in the direction toward the distal end side.

The present invention (7) relates to the catheter according to any one of (1) to (6), wherein the catheter is a balloon catheter.

The present invention (8) relates to the catheter according to any one of (1) to (6), wherein the catheter is a penetrating catheter for penetration in the stenotic lesion of body cavity.

The present invention (9) relates to the catheter according to any one of (1) to (6), wherein the catheter is an injection catheter allowing administration of a treatment substance to a local site in the body cavity.

Advantageous Effects of the Invention

An object of the present invention is to provide a catheter improved in the convenience of operation when the catheter is inserted into the body along a guide wire from outside that is resistant to excessive elongation and deformation of the shaft even under unexpected condition and eliminates the concern about the damage of the shaft, blood vessel, or the like by the proximal end of the core wire without complication of processing or increase in production cost.

EXPLANATION OF REFERENCES

Figure 1:
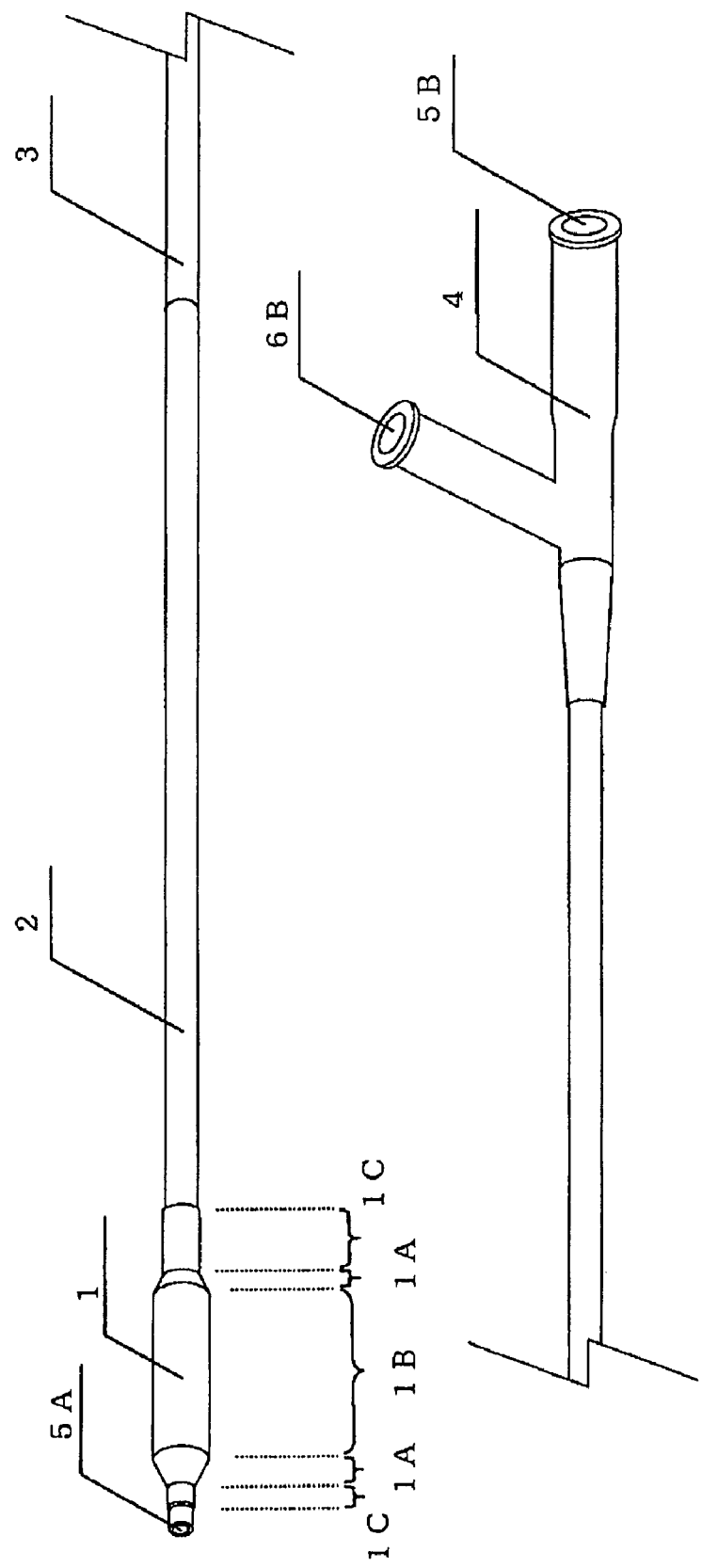
FIG. 1 is a schematic perspective view illustrating an over-the-wire catheter (OTW catheter), one of common balloon catheters.
Figure 2:
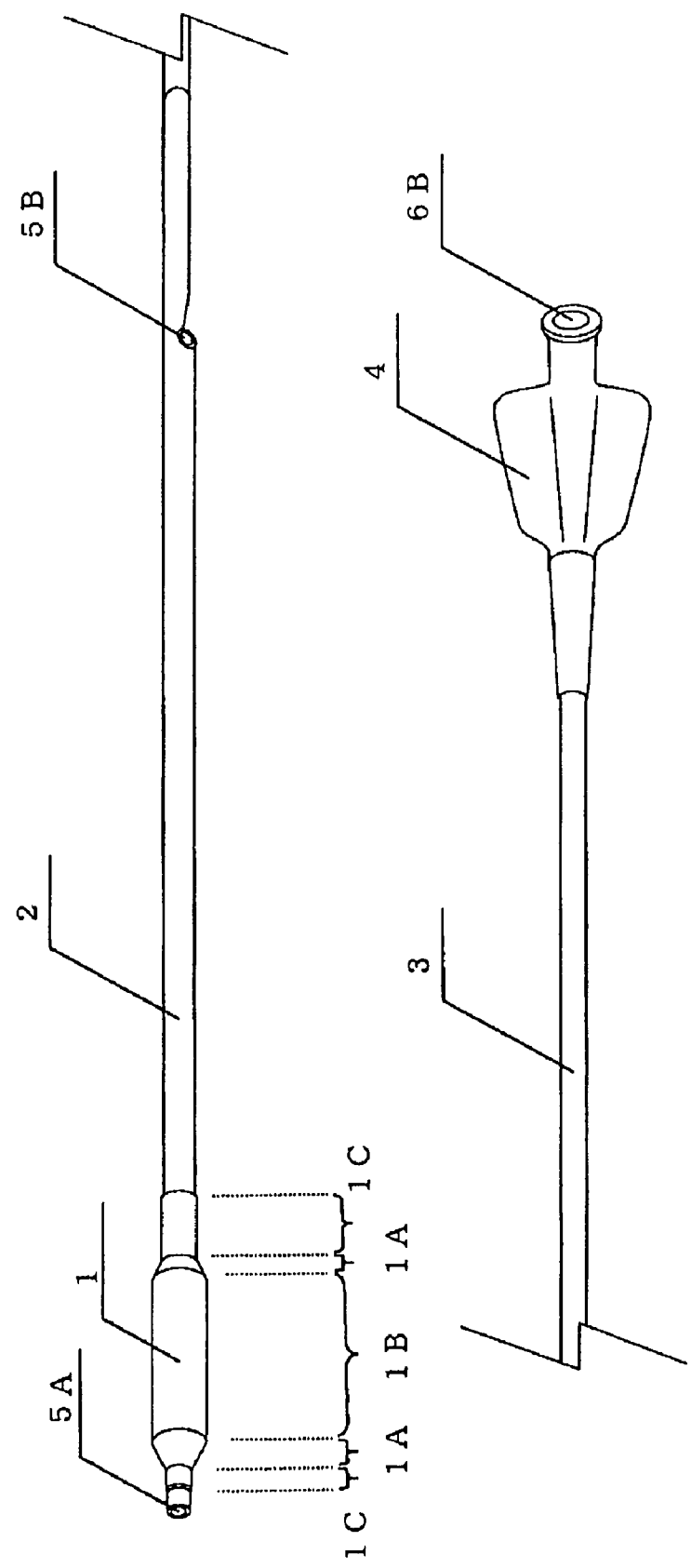
FIG. 2 is a schematic perspective view illustrating a rapid exchange catheter (RX catheter), one of common balloon catheters.

1 Balloon
1A Balloon tapered region
1B Balloon straight tube region
1C Balloon-connecting region
2 Distal-end-sided shaft
2A Distal-end-sided shaft distal region
2B Distal-end-sided shaft proximal region
3 Proximal-end-sided shaft
4 Hub
5 Guide wire lumen
5A Distal opening of guide wire lumen
5B Proximal opening of guide wire lumen
6 Second lumen
6B Proximal opening of second lumen
7 Radiopaque marker
8 External tube
9 Internal tube
10 Dual lumen tube
11 Core wire
11A Core-wire distal end region
11B Core-wire middle region
11C Core-wire proximal terminal
12 Core-wire connecting region
13 Injection hole

BEST MODE OF CARRYING OUT THE INVENTION

Hereinafter, various favorable embodiments of the catheter according to the present invention will be described in detail, with reference to drawings, taking a balloon catheter as the primary example.

The catheter according to the present invention is a rapid exchange catheter (RX catheter) having its guide wire lumen only in the distal end side of the catheter and its proximal opening of the guide wire lumen in the middle of the distal-end-sided shaft. The distal-end-sided shaft consists of the distal-end-sided shaft proximal region in the proximal end side of the distal-end-sided shaft more proximal than the proximal opening of the guide wire lumen (hereinafter, referred to as "distal-end-sided shaft proximal region") and the distal-end-sided shaft distal region of the distal-end-sided shaft more distal than the proximal opening of the guide wire lumen (hereinafter, referred to as "distal-end-sided shaft distal region").

Figure 3:
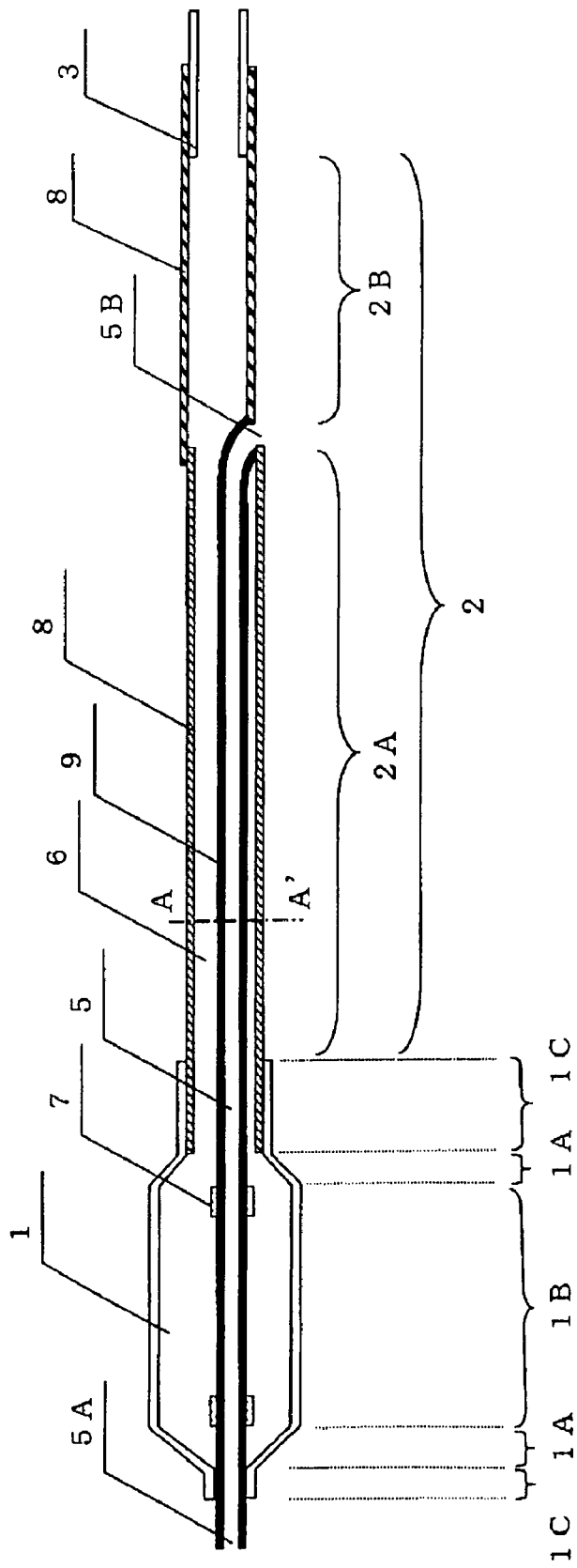
FIG. 3 is a partial schematic side view illustrating the vertical cross section of a common RX balloon catheter having a coaxial structure in the distal-end-sided shaft distal region.
Figure 4:
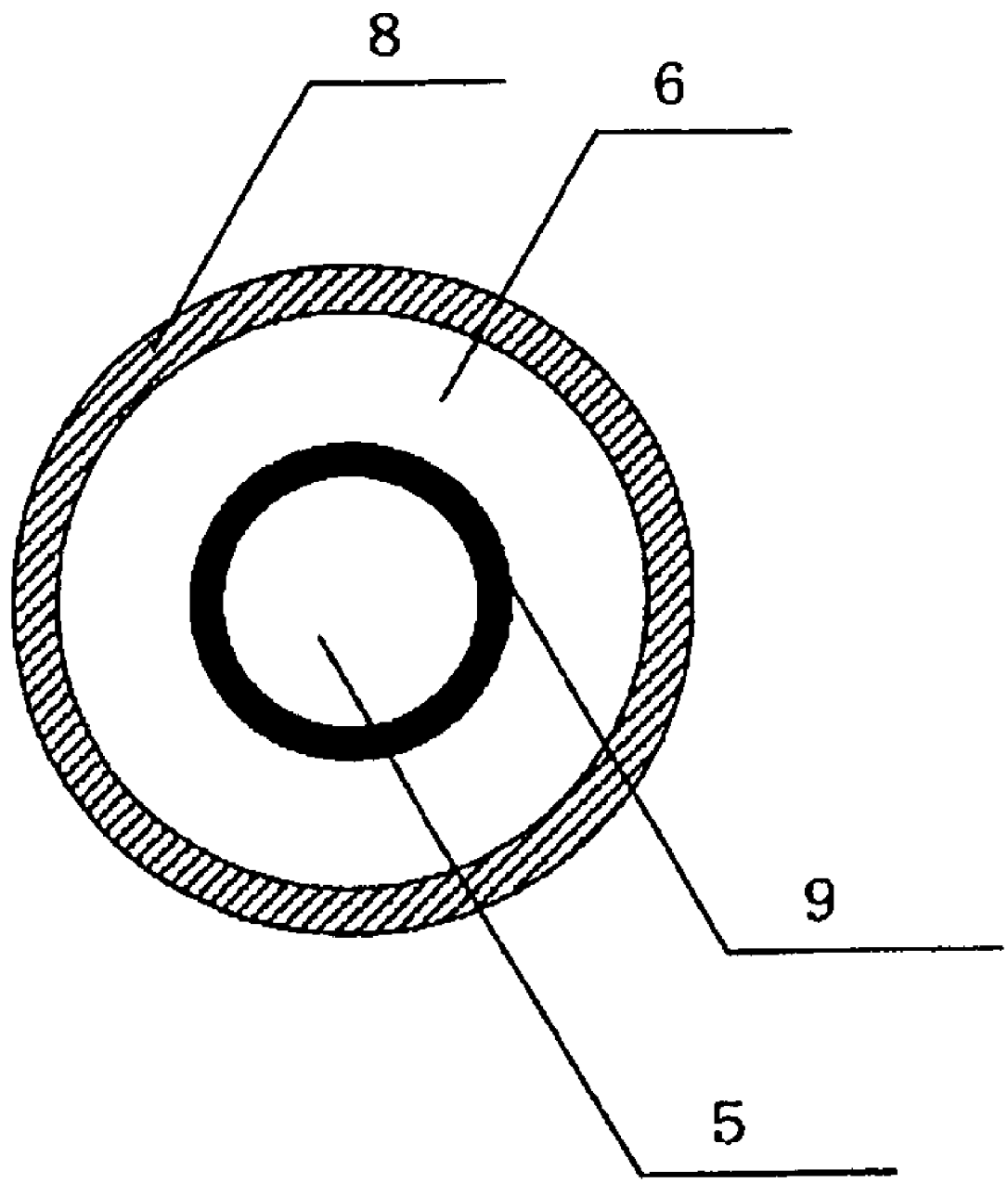
FIG. 4 is a sectional view illustrating the cross section of the catheter of FIG. 3 along the line A-A'.
Figure 5:
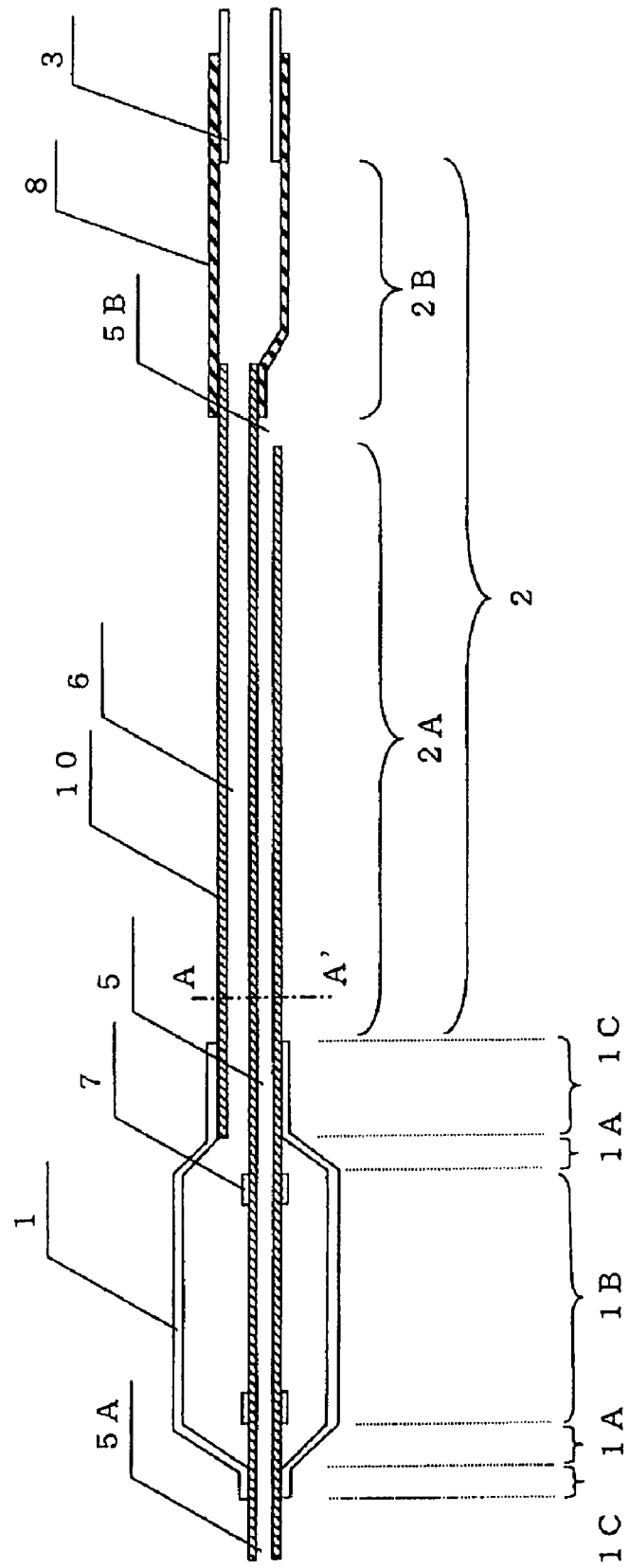
FIG. 5 is a partial schematic side view illustrating the vertical cross section of a common RX balloon catheter having a biaxial structure in the distal-end-sided shaft distal region.
Figure 6:
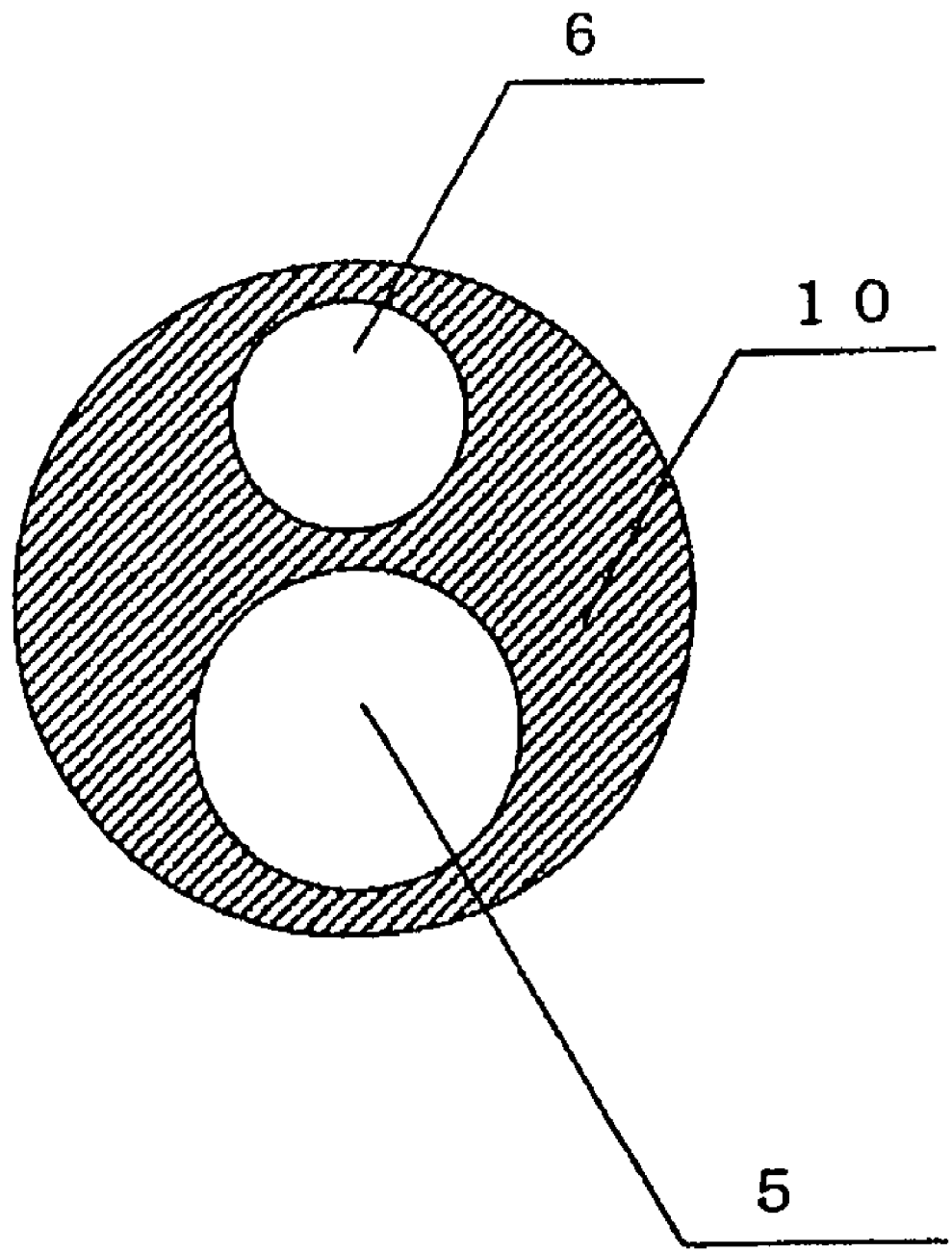
FIG. 6 is a sectional view illustrating the cross section of the catheter of FIG. 5 along the line A-A'.

In such a case, the distal-end-sided shaft distal region is not particularly limited in its structure, if it has a guide wire lumen. Thus as shown in FIGS. 3 and 4, the distal-end-sided shaft distal region may have a coaxial structure of two coaxial tubes, having a guide wire lumen partitioned by the internal surface of the internal tube and a second lumen partitioned by the internal surface of the external tube and the outside surface of the internal tube. When the catheter is a balloon catheter, the second lumen is an inflation lumen, and, when the catheter is an injection catheter, it is an infusion lumen. As shown in FIGS. 5 and 6, the catheter may have biaxial structure in which the guide wire lumen and the second lumen are aligned in parallel. The structure of the catheter is not limited, and may be any other structure, if it does not impair the advantageous effects of the invention.

The catheter according to the present invention characteristically has a proximal opening of the guide wire lumen in the middle of the distal-end-sided shaft and a core wire adjusting the flexibility of the proximal-end-sided distal shaft so that the proximal-end-sided distal shaft becomes harder than the distal-end-sided shaft distal region and softer than the proximal-end-sided shaft in the catheter; and the core wire is connected to the distal-end-sided shaft in the area close to the proximal opening of the guide wire lumen and in a region of the proximal-end-sided core shaft in the catheter.

When the core wire is connected to the distal-end-sided shaft only in the area close to the proximal opening of the guide wire lumen, if the lubricity between the guide wire and the catheter drops distinctively for example by deposition of thrombus during use of the catheter, a tension in the axial direction is applied to the catheter itself when a force is applied to the proximal-end-sided shaft for sliding or withdrawing the catheter. The tension may cause elongation and deformation of the proximal end of the distal-end-sided shaft and the proximal end of the core wire present in the proximal-end-sided shaft may move to the position of the proximal end of the distal-end-sided shaft. In such a case, there are concerns about damage of the proximal end of the distal-end-sided shaft elongated or deformed by the proximal end of the core wire and damage, for example, of blood vessel by the proximal end of the core wire penetrating through the proximal end of the distal-end-sided shaft. In addition, there is also a concern about the damage of the proximal end of the distal-end-sided shaft leading to breakage of the catheter and residual of the fragments thereof in the body cavity.

However, as described above in the present invention, when the core wire is connected to the distal-end-sided shaft in the area close to the proximal opening of the guide wire lumen and in part of the distal-end-sided shaft proximal region, even if a tension in the axial direction is applied to the catheter itself by the same phenomenon, the proximal end of the distal-end-sided shaft in the area where the core wire is connected to the distal-end-sided shaft is not elongated or deformed. The connecting region of the core wire in the distal-end-sided shaft proximal region is preferably closer to the proximal-end-sided shaft in the range that does not impair the other properties of the catheter, to make the length of the proximal end of the distal-end-sided shaft, which may be elongated or deformed, as short as possible when a tension in the axial direction is applied. The distance between the most distal end of the proximal-end-sided shaft and the center of the connecting region of the core wire in the distal-end-sided shaft proximal region is preferably 0 to 30 mm, more preferably 0 to 10 mm.

The core wire is connected to the distal-end-sided shaft in the area close to the proximal opening of the guide wire lumen and in part of the distal-end-sided shaft proximal region. The distance between the center of the connecting region of the core wire in the area close to the proximal opening and the opening is not particularly limited if the advantageous effects of the present invention is preserved, but the center is preferably within 15 mm from the opening in the distal or proximal end side, for altering the flexibility of the catheter as continuously as possible in the length direction.

If the catheter has a structure coaxial in the distal-end-sided shaft distal region, the connecting region in the proximal opening of the guide wire lumen may have a structure in which the region forms a core-wire connecting region including the core wire, as shown in FIGS. 7 to 11, as they are connected to each other by addition of an adhesive into the space between the internal surface of the distal-end-sided shaft and the core wire (between the internal surface of the external tube and outside surface of the internal tube), or alternatively, a structure in which the region forms a core-wire connecting region including the core wire, as they are connected to each other by addition of a melted resin into the space between the internal surface of the distal-end-sided shaft (between the internal surface of the external tube and outside surface of the internal tube) and the core wire. However, for reduction in diameter of the core-wire connecting region and simplification of processing, the structure having a core-wire connecting region formed with a melted resin is preferable, and the internal surface of the external tube and outside surface of the internal tube are preferably made of a thermoplastic resin.

Also in the biaxial catheters shown in FIGS. 12 to 16, a core-wire connecting region including the core wire may be formed by addition of an adhesive into the space between one lumen of the dual lumen tube and the core wire, or alternatively, a core-wire connecting region including the core wire may be formed by addition of a melted resin. For the same reason for the coaxial catheter, the structure having a core-wire connecting region formed with a melted resin is preferable.

Figure 11:
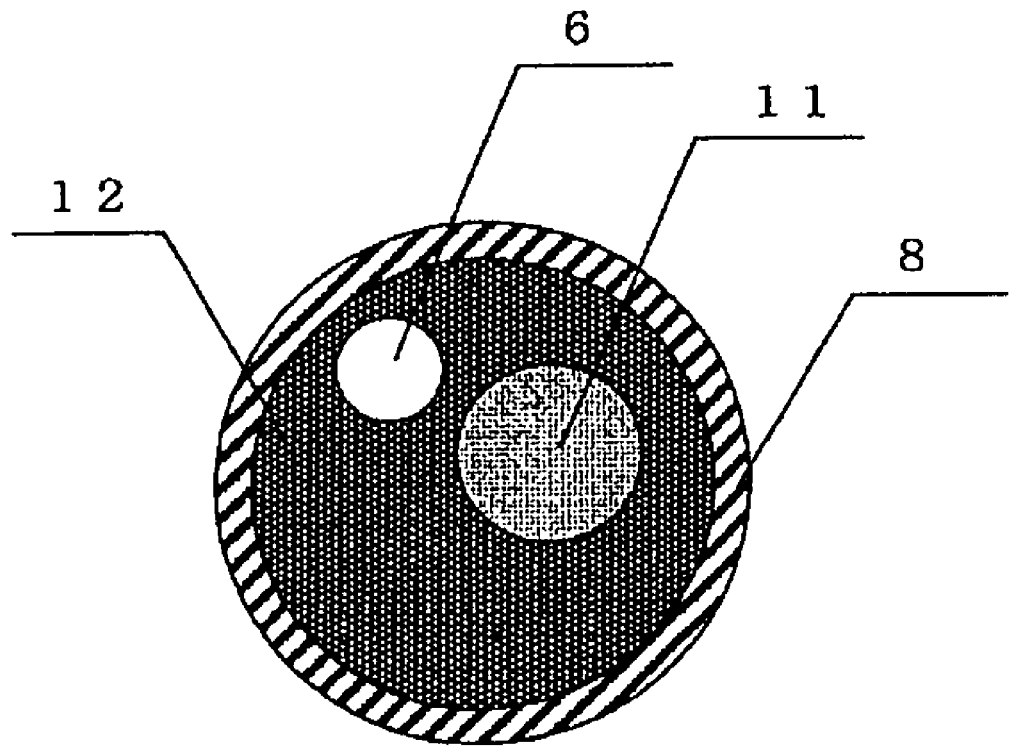
FIG. 11 is a sectional view illustrating the cross section of the catheter of FIG. 7 along the line D-D'.
Figure 16:
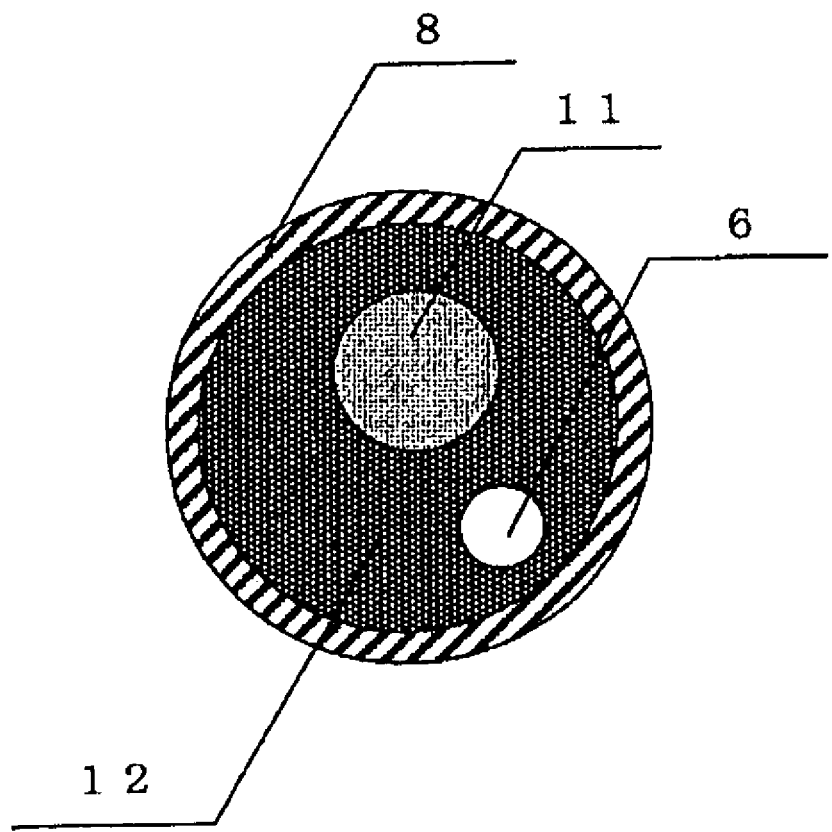
FIG. 16 is a sectional view illustrating the cross section of the catheter of FIG. 12 along the line D-D'.

If the guide wire lumen is not present in the distal-end-sided shaft proximal region, the distal-end-sided shaft proximal region is generally made of a single lumen tube. Thus as shown in FIGS. 11 and 16, the connecting region in part of the proximal end of the distal-end-sided shaft may have a structure in which a core-wire connecting region including the core wire is formed by addition of an adhesive into the space between the internal surface of a single lumen tube constituting the proximal end of the distal-end-sided shaft and the core wire, or a structure having a core-wire connecting region including the core wire formed by addition of a melted resin. For the same reason for the connecting region in the area close to the proximal opening of the guide wire lumen, the structure having a core-wire connecting region formed by addition of a melted resin is preferable.

In any structure of the core-wire connecting region, the second lumen in the core-wire connecting region should be formed, depending on application of the catheter. The second lumen is essential, because it is an inflation lumen when the catheter is a balloon catheter and an infusion lumen when the catheter is an injection catheter. When the second lumen is needed, the core-wire connecting region should be formed, while a core material in any dimension and shape is inserted. In such a case, considering removal of the core material after processing, the external surface of the core material is preferably inactivated by coating with a fluorine resin such as polytetrafluoroethylene, poly-para-xylylene, poly-monochloro-para-xylylene, or the like. Although a core material having an almost circular cross-sectional shape is used and the cross-sectional shape of the lumen formed is almost circular in the examples of FIGS. 9, 11, 14, and 16, the cross-sectional shape of the core material for use is not particularly limited, if the advantageous effects of the present invention is preserved. Thus, a core material in almost rectangular, elliptic, or other shape may be used for processing, considering the processability in production, the sectional area of the desirable lumen, and others. On the other hand, the second lumen in the core-wire connecting region may be absent if the catheter is a penetrating catheter.

The core wire is connected to the distal-end-sided shaft in the area close to the proximal opening of the guide wire lumen and in part of the distal-end-sided shaft proximal region, and is not connected to the proximal-end-sided shaft. Thus, the step of connecting the core wire to the proximal-end-sided shaft disclosed in Patent Document 2 (e.g., by brazing or laser bonding) can be eliminated, allowing simplification of the production process and reduction in production cost.

Figure 7:
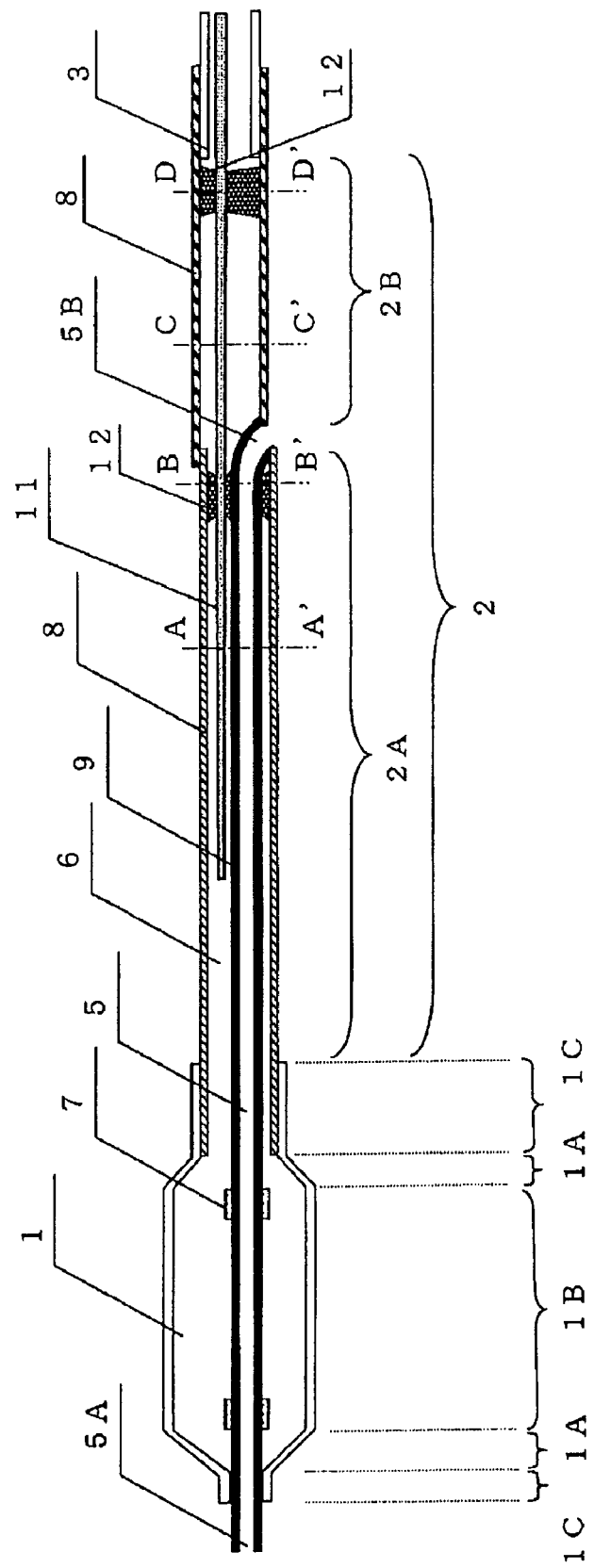
FIG. 7 is a partial schematic side view illustrating the vertical cross section of the RX balloon catheter in an example of the present invention having a coaxial structure in the distal-end-sided shaft distal region.
Figure 8:
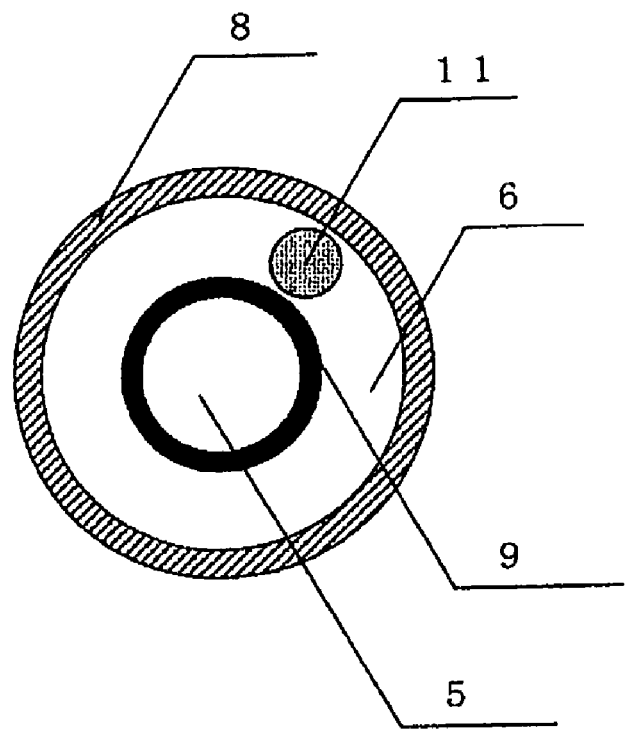
FIG. 8 is a sectional view illustrating the cross section of the catheter of FIG. 7 along the line A-A'.
Figure 9:
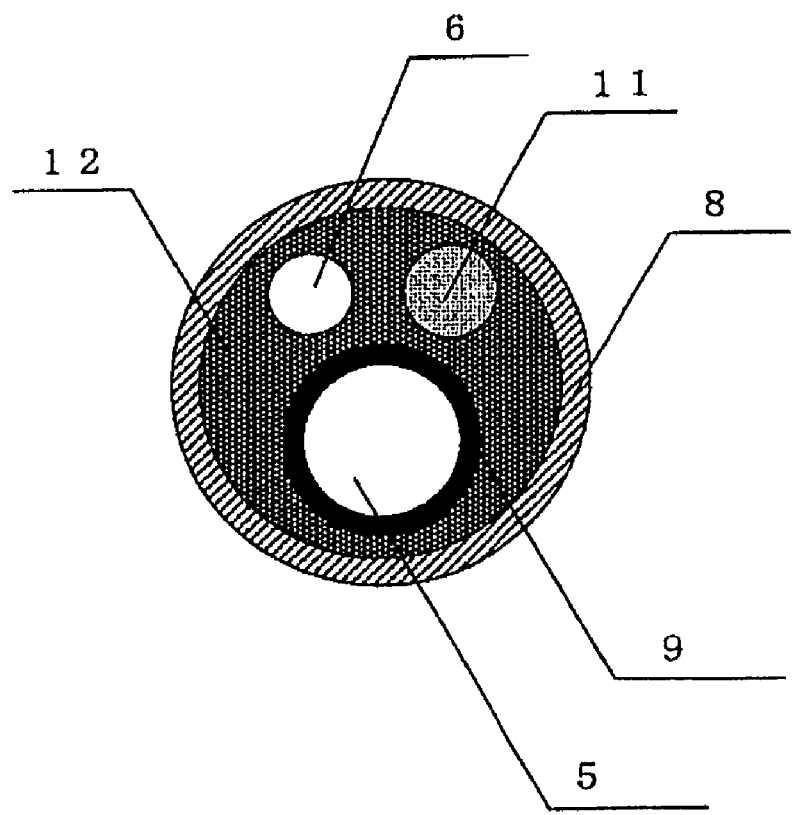
FIG. 9 is a sectional view illustrating the cross section of the catheter of FIG. 7 along the line B-B'.
Figure 10:
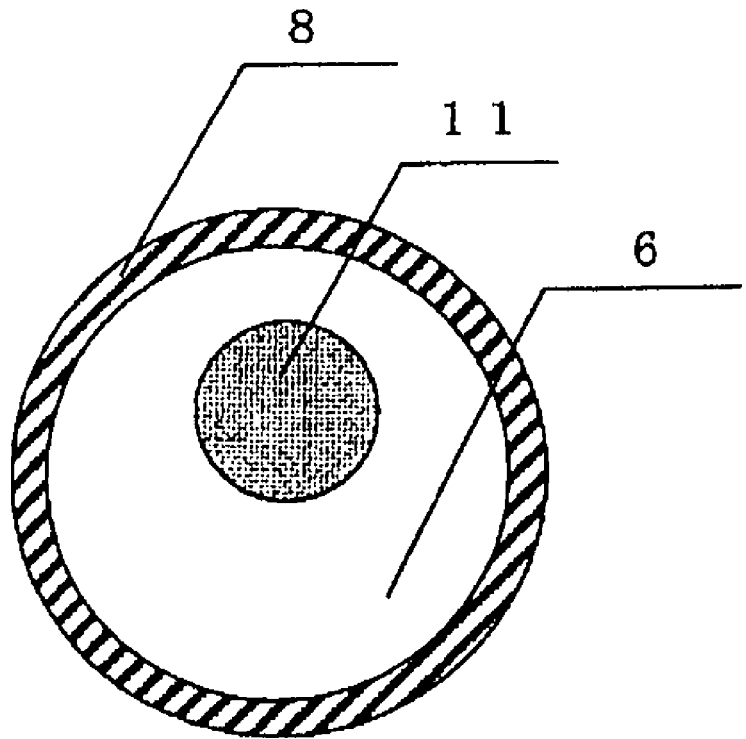
FIG. 10 is a sectional view illustrating the cross section of the catheter of FIG. 7 along the line C-C'.
Figure 12:
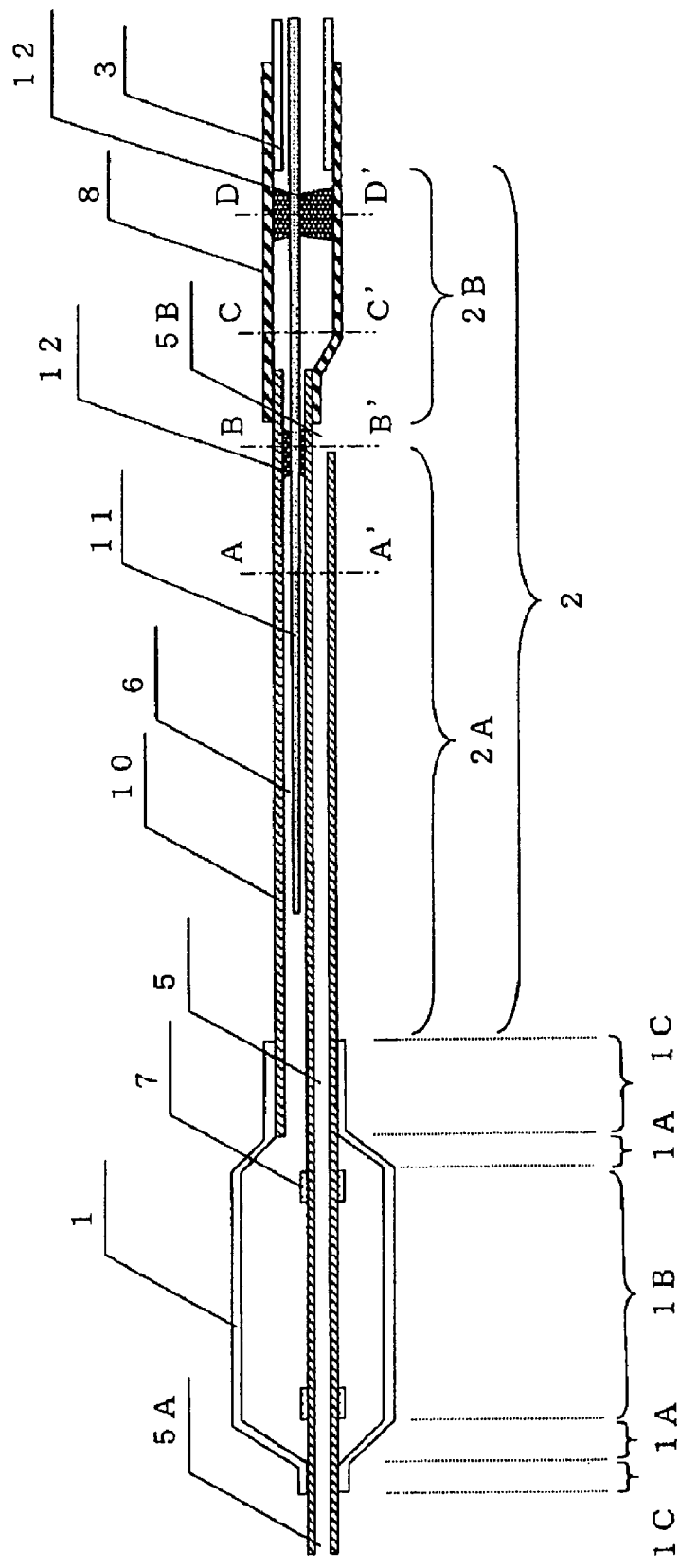
FIG. 12 is a partial schematic side view illustrating the vertical cross section of the RX balloon catheter in an example of the present invention having a biaxial structure in the distal-end-sided shaft distal region.
Figure 13:
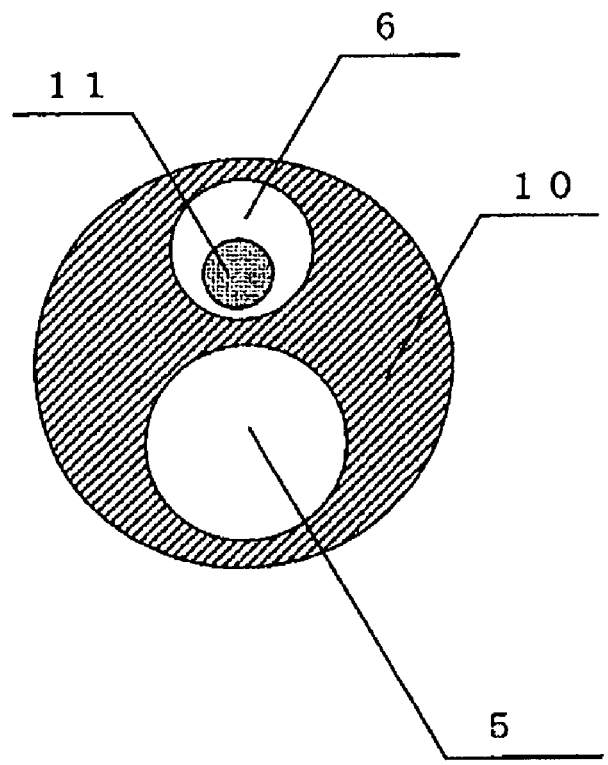
FIG. 13 is a sectional view illustrating the cross section of the catheter of FIG. 12 along the line A-A'.
Figure 14:
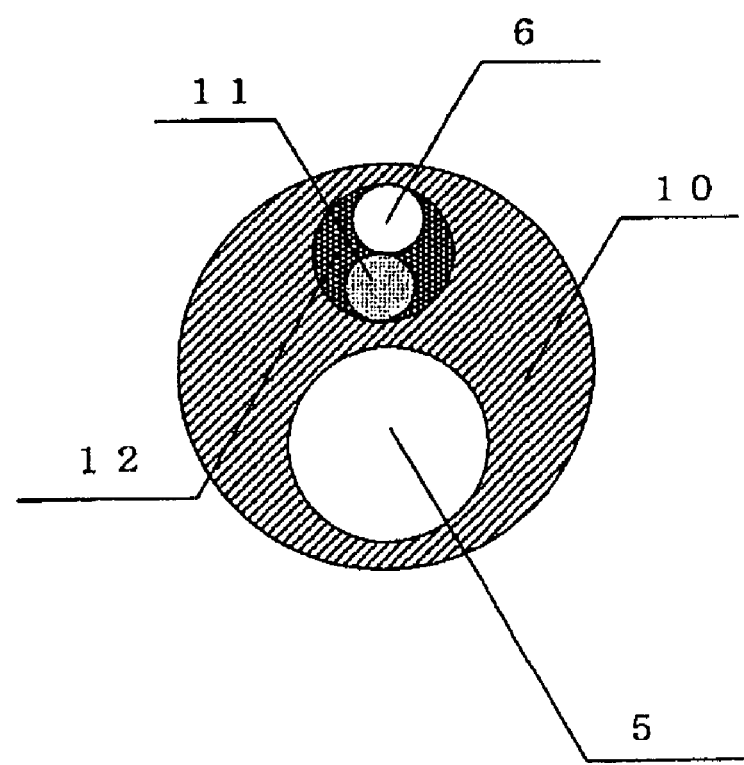
FIG. 14 is a sectional view illustrating the cross section of the catheter of FIG. 12 along the line B-B'.
Figure 15:
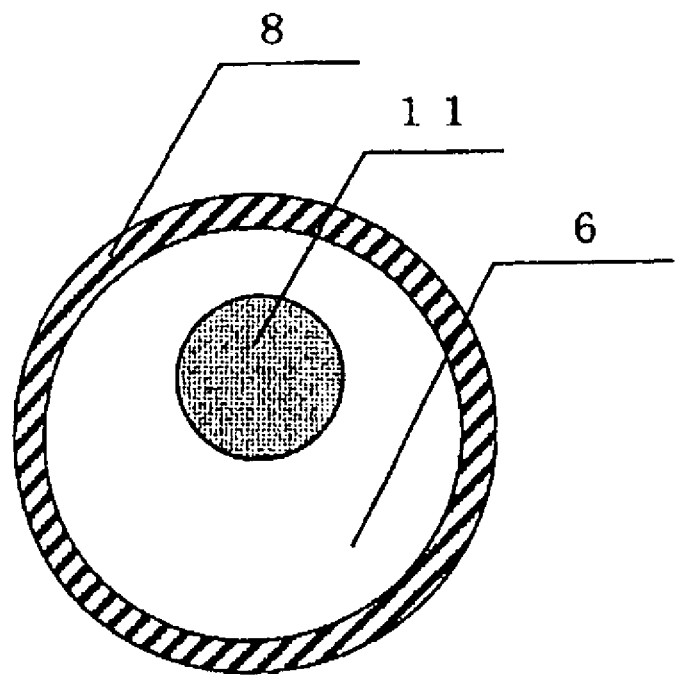
FIG. 15 is a sectional view illustrating the cross section of the catheter of FIG. 12 along the line C-C'.

It is known for those skilled in the art that the convenience of operation during insertion of a catheter along a guide wire depends on the continuity in the rigidity of the catheter in the length direction. Presence of a region where the rigidity is discontinuous raises a concern about kink (bend) of the catheter when it is pushed forward into the body along the guide wire. In addition, a force applied by the surgeon does not reach the distal end of catheter efficiently, and thus, the catheter passes through the stenotic lesion drastically inefficiently. For prevention of the kink described above, the core wire preferably extends to the distal end side beyond the proximal opening of the guide wire lumen, as shown in FIGS. 7 and 12.

When the catheter according to the present invention is a balloon catheter, the lumen in the proximal-end-sided shaft constitutes the second lumen, i.e., an inflation lumen, and thus, the inflation lumen becomes narrower and the response of the balloon to inflation and deflation decreases, as the length of the core wire extending in the proximal-end-sided shaft is elongated. Alternatively when the catheter according to the present invention is an injection catheter, the lumen in the proximal-end-sided shaft constitutes the second lumen, i.e., an infusion lumen, and thus, the infusion lumen becomes narrower and the efficiency of infusing a medical substance decreases, as the length of the core wire extending in the proximal-end-sided shaft is elongated. Thus for achieving the object of the present invention, the core wire is preferably extends into the proximal-end-sided shaft to some extent and does not reach the end of the proximal-end-sided shaft. Thus preferably, the core wire has its proximal terminal, and the proximal terminal is placed inside the proximal-end-sided shaft and in the region of the distal end side of the proximal terminal of the proximal-end-sided shaft to a particular length.

The length of the core wire extending in the proximal-end-sided shaft is preferably so decided that the proximal end of the core wire does not penetrate out of the proximal-end-sided shaft even when the elongatable/deformable distal-end-sided shaft proximal region is elongated to the maximum, considering the length of the proximal region of the elongatable/deformable distal shaft when a tension in the axial direction is applied to the catheter. It is preferably decided, considering the response of the balloon to inflation and deflation, i.e., the capacity inside the balloon and the sectional area of the inflation lumen in the distal-end-sided shaft or proximal-end-sided shaft, when the catheter is a balloon catheter, and alternatively, considering the physical properties of the treatment substance (viscosity, etc.) and the amount thereof, the sectional area of the infusion lumen in distal-end-sided shaft or proximal-end-sided shaft, and others, when the catheter is an injection catheter.

When the distance from the most distal end of the proximal-end sided shaft to the center of the connecting area of the core wire at the proximal end of the distal-end-sided shaft is 0.0 to 30 mm, the length of the core wire extending in the proximal-end-sided shaft is preferably 5 to 300 mm; and, when the distance from the most distal end of the proximal-end-sided shaft to the center of the connecting area of the core wire at the proximal end of the distal-end-sided shaft is 0 to 10 mm, the length of the core wire extending in the proximal-end-sided shaft is preferably 5 to 100 mm.

Patent Document 3 discloses a prior art in which a reinforcement stylet extends from the area close to the proximal terminal of the catheter shaft to the proximal terminal side of the balloon, and the base region of the reinforcement stylet is included in the hub region in the preferable embodiments thereof. Because the reinforcement stylet extends in most of the inflation lumen region in this prior art, it is needed to enlarge the diameter of the catheter shaft for improvement in response of the balloon to inflation and deflation. However, in the present invention, it is possible to shorten the length of the core wire extending in the proximal-end-sided shaft, and thus, advantageously, it is possible to reduce the diameter of the distal-end-sided shaft and the proximal-end-sided shaft without sacrifice of the response of the balloon to inflation and deflation and improve the convenience of operating the balloon catheter drastically by reduction of the diameter.

The roles of the core wire are to improve the convenience of operation in inserting the catheter into the body along the guide wire, transmit the force applied to the catheter and prevent kink (bend) of the catheter. Importantly for that purpose, the catheter should have a rigidity distribution continuous in the length direction. It is possible to make the rigidity more continuous, particularly by forming part of the core wire present in the distal-end-sided shaft proximal region in a tapered structure in which the external diameter thereof is decreasing in the direction toward the distal end. In the case of the example shown in FIG. 17, the core-wire middle region is preferably present at the position in the distal-end-sided shaft proximal region.

The guide wire lumen extends in the area from the distal opening to the proximal opening of the catheter. The proximal opening of the guide wire lumen is formed in the middle of the distal-end-sided shaft. The guide wire lumen preferably extends to distal end side beyond the proximal-end-sided shaft by the length of the distal-end-sided shaft proximal region, for changing the flexibility of the catheter continuously in the length direction, but, in such a case, the length of the distal-end-sided shafts, i.e., the length of the distal end of the distal-end-sided shaft and the proximal end of the distal-end-sided shaft, is not particularly limited, and can be selected according to application site of the catheter. For example, when the catheter is a PTCA balloon catheter, the length of the distal-end-sided shaft is 100 to 600 mm, preferably 200 to 500 mm, and the length of the distal-end-sided shaft distal region (approximately, length of guide wire lumen) is 50 to 450 mm, preferably 150 to 350 mm. The length of the proximal end of the distal-end-sided shaft is 50 to 300 mm, preferably 50 to 200 mm. The length of respective regions may be adjusted in the range above according to application of the balloon catheter. When the catheter is a penetrating catheter or an injection catheter, the length thereof is also adjustable according to application.

The internal and external diameters of distal-end-sided shafts, i.e., distal-end-sided shaft distal region, distal-endsided shaft proximal region, and proximal-end-sided shaft, are also not particularly limited. The external diameter of any region is preferably smaller because the load to the patient to be treated becomes smaller; but, when the catheter is a balloon catheter, it should be decided, taking into consideration the sectional area in the diameter direction and the cross-sectional shape of the inflation lumen, which has a great influence on the response of balloon to inflation and deflation, pressure withstanding strength of the distal-end-sided shaft and the proximal-end-sided shaft, the rigidity of the distal-end-sided shaft, proximal-end-sided shaft and core wire, and others. For example in the case of a PTCA balloon catheter, the external diameter of the distal-end-sided shaft distal region and the distal-end-sided shaft proximal region is 0.75 to 1.10 mm, preferably 0.80 to 0.95 mm. The external diameter of the proximal-end-sided shaft 3 is 0.50 to 1.50 mm, preferably 0.60 to 1.20 mm.

Figure 17:
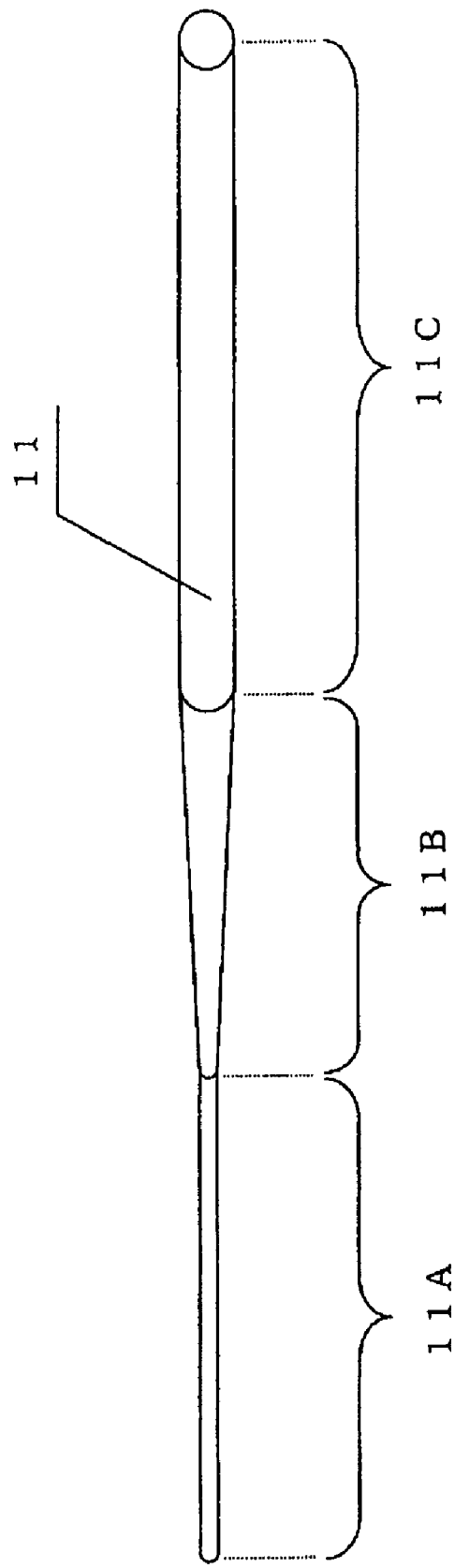
FIG. 17 is a schematic perspective view illustrating an embodiment of the core wire according to the present invention.

The flexibility of the core wire is so adjusted that the distal-end-sided shaft proximal region becomes harder than the distal-end-sided shaft distal region and softer than the proximal-end-sided shaft. The shape and dimension of the core wire may be determined, for example, according to the dimension of and the material for the distal-end-sided shaft and the proximal-end-sided shaft, and application of the catheter. FIG. 17 shows an example of the shape of the core wire, but the shape and the dimension of the core wire is not limited by the Example. In the example shown in FIG. 17, a tapered core-wire middle region with its external diameter shrinking in the direction toward the distal end is preferably placed inside the distal-end-sided shaft proximal region. Preferably, the core-wire distal end region is placed inside the distal-end-sided shaft distal region; the proximal terminal of the core-wire distal end region is connected in the area close to the proximal opening of the guide wire lumen; and the core-wire proximal terminal is connected in part of the proximal end of the distal-end-sided shaft. When the catheter is a PTCA balloon catheter, the core-wire distal end region has an external diameter of 0.08 to 0.30 mm and a length of 20 to 200 mm, preferably an external diameter of 0.10 to 0.25 mm and a length of 30 to 150 mm, and the core-wire proximal terminal has an external diameter of 0.20 to 0.50 mm and a length of 20 to 200 mm, preferably an external diameter of 0.25 to 0.40 mm and a length of 30 to 150 mm. The core-wire middle region has a length of 10 to 100 mm, preferably 20 to 80 mm, and the external diameter thereof is preferably the same as that of the core-wire distal end region and the core-wire proximal terminal.

The material for the core wire is not particularly limited if it is a metal, and may be selected for example according to the dimension and material for the distal-end-sided shaft and the proximal-end-sided shaft and application of the balloon catheter, but is preferably stainless steel or a nickel titanium alloy, from the points of processability and safety to the body. The method of forming a tapered region such as core-wire middle region and a thin diameter region such as core-wire distal end region in the core wire is also not particularly limited, and any known method such as centerless grinding may be used favorably.

When the catheter is a balloon catheter, the methods of producing the balloon inflation/deflation by regulation of the internal pressure include dip molding, blow molding, and others, and a suitable method is selected according to application. When the catheter is a PTCA balloon catheter, blow molding is preferable for sufficient pressure withstanding strength. An example of the method of producing a balloon by blow molding will be described below. A tubular parison in any size is first prepared for example by extrusion molding.

The tubular parison is placed in a mold having a shape identical with the balloon shape, and stretched in the axial direction and in the diameter direction in a biaxial stretching step. The biaxial stretching may be performed under heat multiple times. In addition, stretching in the axial direction may be performed simultaneously with stretching in the diameter direction, or alternatively, before or after that. The product may be annealed for stabilization of the shape and dimension of the balloon.

The balloon has a straight tube region, connecting regions in the distal and proximal end sides, and tapered regions between the straight tube region and the connecting regions. The dimension of the balloon is decided properly according to application of the balloon catheter, but the external diameter of the straight tube region when the balloon is dilated by regulation of internal pressure is 1.50 to 35.00 mm, preferably 1.50 to 30.00 mm, and the length of the straight tube region is 5.00 to 80.00 mm, preferably 7.00 to 60.00 mm.

The resin for the tubular parison is not particularly limited, and examples thereof for use include polyolefin, polyolefin elastomer, polyester, polyester elastomer, polyamide, polyamide elastomer, polyurethane and polyurethane elastomer, and the like, and the resin may be a polymer blend of two or more of these resins or a material having a multilayer structure of two or more resins.

The material for the distal-end-sided shafts, i.e., distal-end-sided shaft distal region or distal-end-sided shaft proximal region, is not particularly limited. When the distal-end-sided shaft distal region has a coaxial structure, examples of the resins for the internal tube include polyolefin, polyolefin elastomer, polyester, polyester elastomer, polyamide, polyamide elastomer, polyurethane, polyurethane-elastomer, and the like; but polyethylene, in particular high-density polyethylene, is preferable, because the guide wire lumen is partitioned by the internal surface of the internal tube; and more preferably, at least part of the internal tube has a multi-layer structure consisting of the innermost layer of high-density polyethylene and the outermost layer of a thermoplastic material that can melt together with the balloon or the external shaft. It is possible to achieve the present invention easily by using the multilayer structure unit as the core-wire connecting region. The internal surface of the internal tube may be coated, for example, with polytetrafluoroethylene for improvement of the slidability of the guide wire.

When the distal-end-sided shaft distal region has a coaxial structure, the material for the external tube is also not particularly limited. Thus, favorably used are polyolefin, polyolefin elastomer, polyester, polyester elastomer, polyamide, polyamide elastomer, polyurethane, polyurethane-elastomer, and the like.

Also when the distal-end-sided shaft distal region has a biaxial structure or a structure other than that, the materials usable for the internal and external tubes described above can be used, and may be, for example, laminated by a known method. Needless to say, the materials described above are also used favorably for the external tube forming the proximal end of the distal-end-sided shaft, and the material and the dimension for the external tube forming the distal-end-sided shaft distal region and the external tube forming the proximal end of the distal-end-sided shaft are selected arbitrarily, taking the distribution in rigidity of the catheter into consideration.

Figure 18:
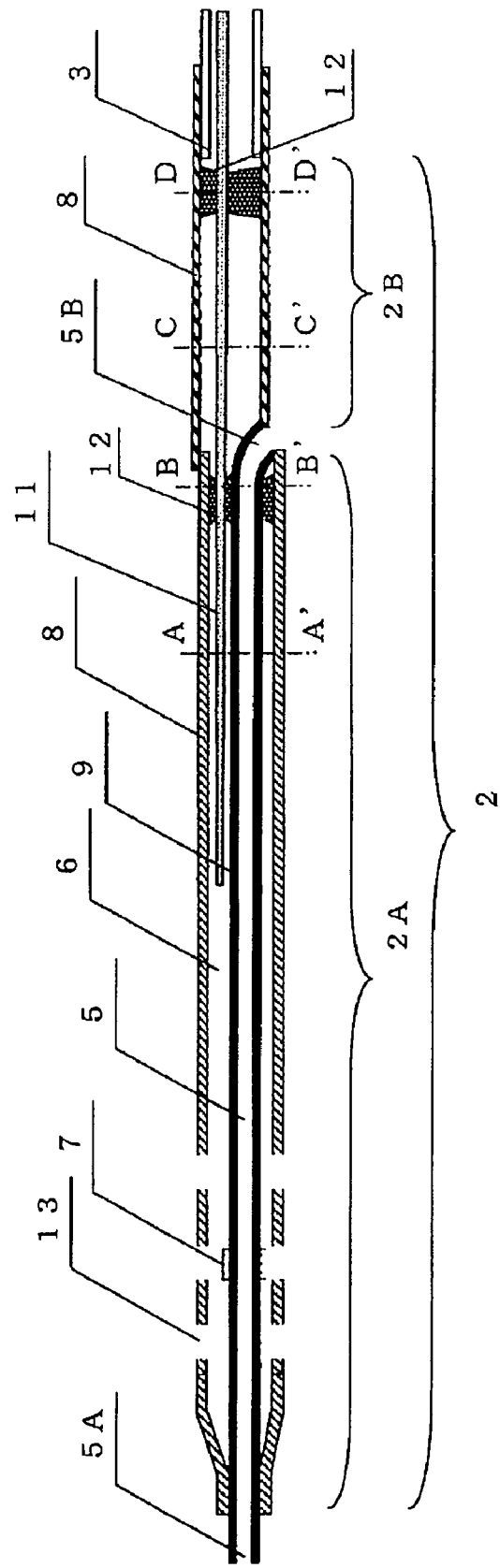
FIG. 18 is a partial schematic side view illustrating the vertical cross section of the RX injection catheter in an example of the present invention having a coaxial structure in the distal-end-sided shaft distal region.

When the catheter is an injection catheter, an injection hole may be formed in the distal-end-sided shaft, as exemplified in FIG. 18. The size, position, number and others of the injection holes are not limited if the advantageous effects of the present invention are preserved, and may be selected arbitrarily according to the properties of the treatment substance. The method of forming the injection hole is also not particularly limited, and examples thereof include machining, laser processing, and the like.

The material for the proximal-end-sided shaft is not particularly limited if it is more rigid than the distal-end-sided shaft, and may be decided according to the dimension and material for the distal-end-sided shaft and application of the catheter, but a metal such as stainless steel or a high-rigidity resin material such as polyimide, polyamide-imide, or polyether ether ketone is preferable, from the points of processability, safety to the body, and others. It is also possible to make the rigidity of the distal end side of proximal-end-sided shaft lower than the proximal end side of proximal-end-sided shaft and the rigidity distribution more uniform, by forming spiral cut, groove, slit, or the like on the distal end side of proximal-end-sided shaft, for more continuous distribution of the rigidity of the catheter in the length direction.

Favorable examples of the materials for the hub include resins such as polycarbonate, polyamide, polyurethane, polysulfone, polyarylate, styrene-butadiene copolymers, and polyolefin.

The method of connecting the connecting regions is not particularly limited, and any known method may be used. Examples thereof include bonding with an adhesive, melting if the regions are made of a thermoplastic material, and the like. When an adhesive is used, the composition, chemical structure, hardening mode of the adhesive are not particularly limited. Thus, adhesives based on urethane, silicone, epoxy, and cyanoacrylate are used favorably from the points of composition and chemical structure, and two-liquid, UV-hardening, water-absorption hardening, or thermosetting adhesives are used favorably from the point of hardening mode. When an adhesive is used, use of an adhesive having a hardness after hardening to the degree that the rigidity of the junction units does not change discontinuously before and after the connection regions is preferable, and the adhesive may be selected according to the material, dimension, rigidity, and others of the connecting regions. The connecting region may be heat-treated for reduction of the diameter of the connecting region, and the connecting region may be treated before bonding with plasma such as of oxygen gas for improvement in adhesiveness if it is a less adhesive material such as polyolefin.

A radiopaque marker may be formed thereon for improvement in visibility of a particular unit in the catheter and for facilitating identification of the location of the catheter, during treatment with the catheter according to the present invention. The kind of the material for the radiopaque marker is arbitrary if it is a material opaque to X ray, and may be a metal or a resin. The position and number thereof installed are also not limited, and may be decided properly according to application of the catheter.

The outside face of the catheter may be hydrophilized by coating, to make insertion thereof into the blood vessel or the guide catheter easier. Thus, at least part of the regions in contact with blood such as the distal-end-sided shaft and the proximal-end-sided shaft may be hydrophilized by coating to make it more slidable when in contact with blood. However, the region and length of the hydrophilic coating are decided properly according to application of the catheter. The kind of the hydrophilic coating is not limited, if the advantageous effects of the present invention is preserved, and favorable examples thereof include hydrophilic polymers such as poly (2-hydroxyethyl methacrylate), polyacrylamide, and polyvinylpyrrolidone, and the coating method is also not limited.

When the catheter is a balloon catheter, the outside face of the balloon may be hydrophobilized by coating, for prevention of balloon slipping when the balloon is dilated, depending on applications. The kind of the hydrophobic coating is not particularly limited, and a hydrophobic polymer such as silicone is used favorably.

EXAMPLES

Hereinafter, typical Examples and Comparative Examples in the present invention will be described in detail, but it should be understood that the present invention is not limited by the following Examples.

Example 1

A tubular parison (internal diameter: 0.43 mm, external diameter: 0.89 mm) was prepared by extrusion molding with a polyamide elastomer (PEBAX7233SA01, manufactured by Elf Atochem), and then, the parison was blow-molded by biaxial stretching, to give a balloon having an external diameter in the straight tube region at 3.0 mm and a length in the straight tube region at 20 mm.

An internal tube (internal diameter: 0.42 mm, external diameter: 0.56 mm, length: 300 mm) and an external tube (internal diameter: 0.71 mm, external diameter: 0.88 mm, length: 450 mm) were formed by extrusion molding with a polyamide elastomer (PEBAX7233SA01, manufactured by Elf Atochem). The balloon and the external tube were bonded to each other by thermal fusion, and the internal tube and the external tube were placed in the coaxial double-tube shape, and the balloon and the internal tube were bonded by thermal fusion. A slit having a length of halfway around the tube in the circumferential direction was formed at a position 260 mm from the terminal of the external tube, and the internal tube was pulled out of the external tube and heat fused in that state, forming a proximal opening of the guide wire lumen, to give a distal-end-sided shaft.

A proximal-end-sided shaft (internal diameter 0.50 mm, external diameter 0.66 mm, length 1,100 mm) was prepared with SUS316L stainless steel. In addition, a core wire in the shape shown in FIG. 17 (external diameter of core-wire distal end region: 0.15 mm, length of core wire distal end: 120 mm, length of core-wire middle region: 80 mm, external diameter of core-wire proximal terminal: 0.35 mm, length of the proximal end of core wire: 150 mm) was prepared with SUS304 stainless steel.

The core wire is so placed in the distal-end-sided shaft that the proximal end of the core-wire distal end region is present at the proximal opening of the guide wire lumen; a polytetrafluoroethylene-coated SUS304 stainless steel core material (external diameter: 0.30 mm) for fixing the inflation lumen was placed; and the composite was placed in a polyamide elastomer tube prepared by extrusion molding (internal diameter: 1.05 mm, external diameter: 1.20 mm) and heat fused, to give a core-wire connecting region. The core-wire connecting region is formed in the area close to the proximal opening of the guide wire lumen and at the position 15 mm from the proximal terminal of the distal-end-sided shaft.

The distal-end-sided shaft and the proximal-end-sided shaft were bonded to each other with a two-liquid urethane-based adhesive (UR0531, manufactured by H. B. Fuller). The area of the distal-end-sided shaft and the proximal-end-sided shaft overlapping each other was 10 mm in width, and the center of the core-wire connecting region in the proximal end side was positioned 5 mm from the distal end of the proximal-end-sided shaft. A hub was formed by injection molding with polycarbonate (Makloron 2658, manufactured by Bayer) and bonded to the proximate terminal of the proximal-end-sided shaft with a two-liquid urethane-based adhesive (UR0531, manufactured by H. B. Fuller). The balloon was wrapped and sterilized with ethyleneoxide gas, to give a balloon catheter. The number of the samples prepared was 3.

Example 2

Figure 19:
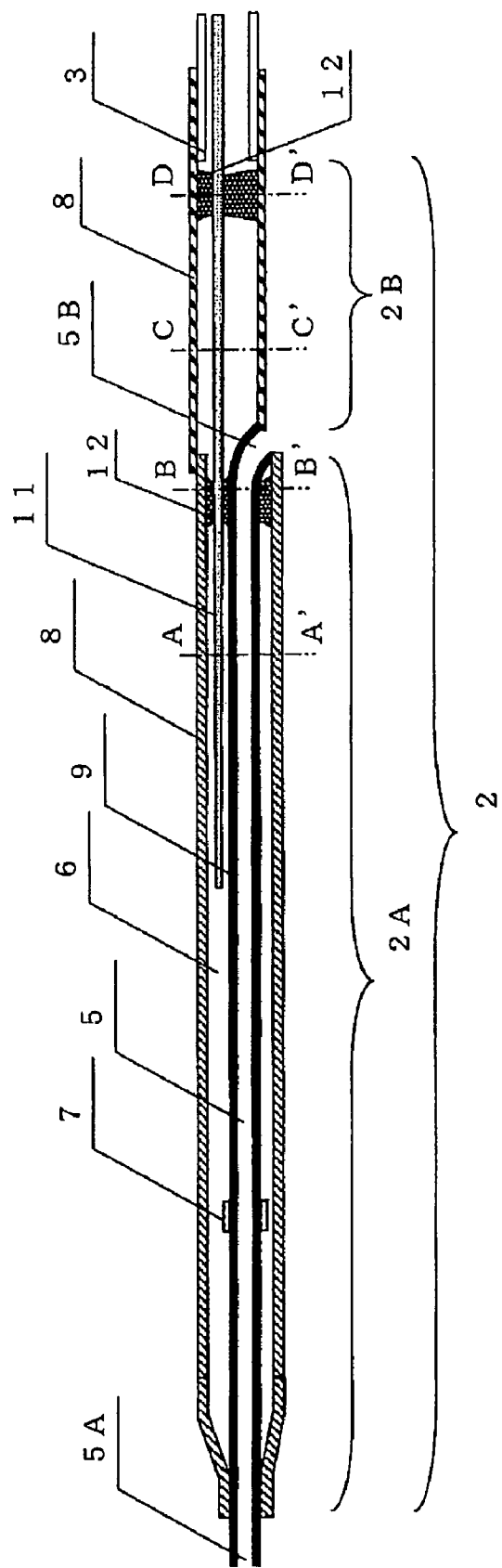
FIG. 19 is a partial schematic side view illustrating the vertical cross section of the RX injection catheter in another example of the present invention having a coaxial structure in the distal-end-sided shaft distal region.

A penetrating catheter was prepared in a similar manner to Example 1, except that the balloon was not connected and the external tube and the internal tube are bonded to each other, as shown in FIG. 19.

Example 3

An injection catheter was prepared in a similar manner to Example 2, except that four holes with a diameter of 100 μm were formed as injection holes in the distal end side of the external tube, as shown in FIG. 18.

Comparative Example 1

A catheter was prepared in a similar manner to Example 1, except that the core-wire connecting region is only the area close to the proximal opening of the guide wire lumen.

Comparative Example 2

A catheter was prepared in a similar manner to Example 2, except that the core-wire connecting region was only the area close to the proximal opening of the guide wire lumen.

Comparative Example 3

A catheter was prepared in a similar manner to Example 3, except that the core-wire connecting region was only the area close to the proximal opening of the guide wire lumen.
(Evaluation)
A commercially available guide wire (external diameter: 0.014") was inserted into each of the guide wire lumens obtained in Examples 1 to 3 and Comparative Examples 1 to 3, and bonded to each catheter in the proximal opening of the guide wire lumen by using a two-liquid urethane-based adhesive (UR0531, manufactured by H. B. Fuller), to give a catheter having a guide wire drastically less slidable in the body. Each catheter was immersed in hot water at 37° C.; the hub was pulled while the proximal opening of the guide wire lumen is held in that state; and the damage on the distal-end-sided shaft formed by the core wire was evaluated.

In all catheters of Comparative Examples 1 to 3, the proximal end of the core wire was located at the position of the elongated and deformed proximal end of the distal-end-sided shaft. In one catheter in Comparative Example 1 and two catheters in Comparative Examples 2 and 3, observed was a phenomenon of the proximal end of the core wire sticking out of the proximal end of the distal-end-sided shaft. However, in the catheters obtained in Examples 1 to 3 according to the present invention, the proximal end of the core wire remained in the proximal-end-sided shaft even when the distal-end-sided shaft was pulled to breakage and there was no damage on the distal-end-sided shaft by the proximal end of the core wire.

The invention claimed is:

1. A catheter, comprising a distal-end-sided shaft of resin tube, a proximal-end-sided shaft more rigid than the distal-end-sided shaft, and a guide wire lumen allowing incorporation of a guide wire inside and having a distal opening and a proximal opening, the guide wire lumen forms the distal opening in the most distal end region of the catheter and the proximal opening in the middle of the distal-end-sided shaft; the distal end region of the proximal-end-sided shaft is connected to the proximal terminal of the distal-end-sided shaft; the distal-end-sided shaft includes the distal-end-sided shaft proximal region and the distal-end-sided shaft distal region; a core wire for adjustment of the flexibility of the distal-end-sided shaft proximal region is so placed in the catheter that the distal-end-sided shaft proximal region becomes harder than the distal-end-sided shaft distal region and softer than the proximal-end-sided shaft; and the core wire is connected to the distal-end-sided shaft adjacent to the proximal opening of the guide wire lumen and in part of the distal-end-sided shaft proximal region, wherein the core wire is connected to the internal surface of the distal-end-sided shaft as it is covered with a thermoplastic resin layer in the area where the core wire is connected to the distal-end-sided shaft.

2. The catheter according to claim 1, wherein the proximal opening of the guide wire lumen is present between the distal-end-sided shaft distal region and the distal-end-sided shaft proximal region.

3. The catheter according to claim 1, wherein the core wire has a distal end region, which is located to the distal end side of the proximal opening of the guide wire lumen.

4. The catheter according to claim 1, wherein at least part of the core wire in the region corresponding to the distal-end-sided shaft proximal region has a tapered shape with its external diameter gradually decreasing in the direction toward the distal end side.

5. The catheter according to claim 1, wherein the catheter is a balloon catheter.

6. The catheter according to claim 1, wherein the catheter is a penetrating catheter for penetration in the stenotic lesion of body cavity.

7. The catheter according to claim 1, wherein the catheter is an injection catheter allowing administration of a treatment substance to a local site in the body cavity.

8. A catheter, comprising a distal-end-sided shaft of resin tube, a proximal-end-sided shaft more rigid than the distal-end-sided shaft, and a guide wire lumen allowing incorporation of a guide wire inside and having a distal opening and a proximal opening, the guide wire lumen forms the distal opening in the most distal end region of the catheter and the proximal opening in the middle of the distal-end-sided shaft; the distal end region of the proximal-end-sided shaft is connected to the proximal terminal of the distal-end-sided shaft; the distal-end-sided shaft includes the distal-end-sided shaft proximal region and the distal-end-sided shaft distal region; a core wire for adjustment of the flexibility of the distal-end-sided shaft proximal region is so placed in the catheter that the distal-end-sided shaft proximal region becomes harder than the distal-end-sided shaft distal region and softer than the proximal-end-sided shaft; and the core wire is connected to the distal-end-sided shaft adjacent to the proximal opening of the guide wire lumen and in part of the distal-end-sided shaft proximal region, wherein the core wire has a distal end region, which is located to the distal end side of the proximal opening of the guide wire lumen, and wherein the core wire extends into the proximal-end-sided shaft to some extent without reaching the end of the proximal-end-sided shaft.

* * * * *